(12) United States Patent
Brenner et al.

(10) Patent No.: US 7,439,463 B2
(45) Date of Patent: Oct. 21, 2008

(54) FOOT SWITCH FOR ACTIVATING A DENTAL OR MEDICAL TREATMENT APPARATUS

(75) Inventors: Tod Brenner, Pine Beach, NJ (US); Kevin Lint, Seven Valleys, PA (US)

(73) Assignee: DENTSPLY International Inc., York, PA (US)

( * ) Notice: Subject to any disclaimer, the term of this patent is extended or adjusted under 35 U.S.C. 154(b) by 396 days.

(21) Appl. No.: 11/333,855

(22) Filed: Jan. 17, 2006

(65) Prior Publication Data

US 2007/0166661 A1 Jul. 19, 2007

(51) Int. Cl.
*H01H 9/06* (2006.01)
(52) U.S. Cl. ..................... 200/86.5; 433/101
(58) Field of Classification Search .............. 200/86.5
See application file for complete search history.

(56) References Cited

U.S. PATENT DOCUMENTS

| | | | |
|---|---|---|---|
| 3,471,928 A | 10/1969 | Billin | |
| 3,980,848 A | 9/1976 | Schultz et al. | |
| 4,041,609 A | 8/1977 | Bresnahan et al. | |
| 4,114,275 A | 9/1978 | Jones et al. | |
| 4,156,187 A | 5/1979 | Murry et al. | |
| 4,184,510 A | 1/1980 | Murry et al. | |
| 4,354,838 A | 10/1982 | Hoyer et al. | |
| 4,417,875 A | 11/1983 | Matsui | |
| 4,798,535 A | 1/1989 | Nielsen | |
| 5,091,656 A | 2/1992 | Gahn | |
| 5,125,837 A | 6/1992 | Warrin et al. | |
| 5,132,498 A | 7/1992 | Lee | |
| 5,419,703 A | 5/1995 | Warrin et al. | |
| 5,423,231 A * | 6/1995 | Helfrich et al. | ............... 74/561 |
| 5,431,645 A | 7/1995 | Smith et al. | |
| 5,535,642 A * | 7/1996 | Moll | ........................... 74/561 |
| 5,754,016 A | 5/1998 | Jovanovic et al. | |
| 6,074,388 A | 6/2000 | Tockweiler et al. | |
| 6,079,687 A | 6/2000 | Calleia | |
| 6,303,884 B1 * | 10/2001 | Hou et al. | ................. 200/86.5 |
| 6,768,425 B2 | 7/2004 | Flaherty et al. | |
| 6,866,507 B2 | 3/2005 | Beerstecher | |

(Continued)

FOREIGN PATENT DOCUMENTS

DE 197 30 456 1/1999

(Continued)

*Primary Examiner*—Anh T. Mai
*Assistant Examiner*—Lheiren Mae A Anglo
(74) *Attorney, Agent, or Firm*—Douglas J. Hura; Daniel W. Sullivan

(57) ABSTRACT

A foot switch device for activating a dental or medical treatment apparatus is provided. The foot switch device is particularly suitable for controlling an ultrasonic dental scaler. The foot switch device includes a base plate; a central housing attached to the base plate; an upper, moveable cover mounted on the housing; and a connecting collar attached to the upper cover for retaining the cover on the housing while allowing the cover to move upwardly and downwardly relative to the housing. The central housing contains a first electrical switch for transmitting a first signal to the apparatus, and a second electrical switch for transmitting a second signal to the apparatus. An operator depresses the upper cover with his or her foot to activate the switching mechanism and control the operation of the dental or medical apparatus.

25 Claims, 15 Drawing Sheets

U.S. PATENT DOCUMENTS

| | | |
|---|---|---|
| 6,893,261 B1 | 5/2005 | Feine |
| 2002/0137007 A1* | 9/2002 | Beerstecher ................ 433/101 |
| 2004/0115591 A1 | 6/2004 | Warner |
| 2005/0080403 A1 | 4/2005 | Takahaski |
| 2005/0147940 A1 | 7/2005 | Mace |

FOREIGN PATENT DOCUMENTS

| | | |
|---|---|---|
| EP | 1 498 082 | 1/2005 |

* cited by examiner

FOOT SWITCH FOR ACTIVATING A DENTAL OR MEDICAL TREATMENT APPARATUS

BACKGROUND OF THE INVENTION

1. Field of the Invention

The present invention relates generally to a foot switch device used for activating a dental or medical treatment apparatus. More particularly, the invention relates to a two-stage foot switch device having an upper moveable cover. An operator depresses the cover with his or her foot to activate the switching mechanism in the foot switch device. The switching mechanism controls the operation of the dental/medical apparatus. The foot switch device is particularly suitable for operating an ultrasonic dental scaler.

2. Brief Description of the Related Art

Today, dental and medical professionals use many instruments that are controlled by foot control systems. For example, surgical cutting instruments, endoscopic tools, irrigation and aspiration tools, dental drills and other handpieces, ultrasonic dental scalers, and dental prophylaxis units can be activated with foot control systems. The foot control system typically includes a foot switch device that is placed on the floor within easy reach of the practitioner. The foot switch is used to activate a dental/medical apparatus, which includes a base-operating unit. The foot switch is typically connected to the base unit by a connector cable in a "hard-wired" system. Alternatively, remote, "wireless" foot control systems, which do not use a connector cable, can be used to activate the base unit in some instances. A flexible, instrument cable connects the dental/medical instrument, for example, a dental handpiece, to the base unit. The dental or medical practitioner activates the base unit and attached dental/medical instrument by depressing the foot switch with his or her foot. Some conventional foot switches are referred to as multi-position or multi-staged switches. An operator depresses the pedal of the foot switch to a certain position, and this action causes the dental/medical apparatus to operate in a specific mode. The particular operational mode is based on the position of the foot switch pedal. For example, with a two-position foot switch, a dental practitioner can depress the pedal to a first position so that water flows through the handpiece for rinsing the teeth of a patient. Then, the pedal of the foot switch can be depressed to a second position so that a cleaning spray flows through the handpiece for cleaning the teeth. Such foot control systems provide several advantages.

First, the foot switch device is easy to use and efficient. The dental/medical professional can activate the instrument attached to the base unit by simply depressing the foot switch with his or her foot. Secondly, the dental/medical practitioner's hands are kept free when working with a foot switch device. The practitioner thus can handle other instruments and accessories while treating the patient. The practitioner is better able to concentrate on performing the needed dental/medical procedure. Thirdly, as mentioned above, some conventional foot switches are used in wireless systems, which do not run a connector cable between the foot switch and base unit. These wireless foot switches are used to remotely activate the base unit and attached dental/medical instruments. Many dental/medical operatory rooms contain numerous long cords, cables, wires, and the like which can become entangled easily. The entangled cords and cables take up space and may cause potential safety hazards. A wireless foot switch system helps minimize some of these hazards.

Foot switch devices can have a wide variety of structures. For example, Bresnahan et al., U.S. Pat. No. 4,041,609 discloses a foot control unit for controlling the operation of dental equipment, particularly air turbine dental handpieces. The foot control unit includes a triangular-shaped base, a body portion that is supported by the base, and a removable cover. Three pivotal pedals project radially from the body portion of the foot switch in the form of a spider-like configuration. The pedals are arranged at evenly spaced positions around the circumference of the base. Each pedal includes a foot-engageable shoe connected to a pedal support member. A dentist may depress any of the pedals, and this action is transmitted to an actuator member, which also has a three arm spider-like configuration. The actuator causes a vertically movable plunger to be depressed and a control unit in the foot switch is activated. An electrical cable extending from the foot control unit to the dental handpiece is used to transmit the switching signal.

Jones et al., U.S. Pat. No. 4,114,275 discloses a foot switch for controlling the flow of compressed air to an air-driven dental handpiece. The foot switch device includes a diaphragm therein for forming an air-sealed chamber, which reduces in volume upon depression of the foot pedal. As the foot pedal is depressed, air is conveyed through an air tube to an air modulating, regulator valve that is positioned away from the foot pedal device. The valve controls the flow of compressed air to the dental handpiece and drives the dental handpiece. Alternatively, the system can include a diaphragm-operated electrical switch that is positioned away from the foot switch for electronically controlling the flow of air to the handpiece.

Matsui, U.S. Pat. No. 4,417,875 discloses a foot controller for controlling the rotational speed of an air turbine dental handpiece. The foot controller is designed such that the front part of the pedal is used for controlling high-speed rotation of the handpiece and requires a relatively small amount of foot pressure, while the rear portion of the pedal is used for controlling low-speed rotation and requires a relatively high amount of foot pressure.

Lee, U.S. Pat. No. 5,132,498 discloses a foot switch comprising a base covered with an upper cover and a press member. The foot switch houses a pressure-contact switch, a pivoting rotary-type actuating member, and compression spring. The press member is pressed down in response to a foot-pressing action. This causes the actuating member to rotate downward so that a hooked portion of the actuating member is pressed against a cylindrical press button, thereby activating the foot switch.

Warrin et al., U.S. Pat. Nos. 5,125,837 and 5,419,703 disclose an ultrasonic dental scaler unit having a handpiece and scaling insert that can be used for scaling teeth and providing therapeutic lavage solutions to periodontal pockets in the mouth. The dental scaler unit includes a foot switch device, which is connected to the base unit by an electrical cable. The scaler unit further includes a dental handpiece, which is connected to the base unit by a conduit containing electrical wires and a tube for cooling water. The base unit includes a switch that can be thrown to a first or second position. The foot switch also can be depressed to a first or second position. The positions of the base unit switch and foot switch make it possible for the practitioner to use the apparatus for scaling only, lavage only, or simultaneous lavage and scaling.

Jovanovic et al., U.S. Pat. No. 5,754,016 discloses an ultrasonic dental scaler system having a base unit, which is connected by a cable to a foot switch device. The scaler handpiece, which is connected to the base unit, includes a feedback coil for controlling the amplitude and vibration of the magnetostrictive scaling insert. The amplitude and frequency of vibration of the tip of the scaling insert can be continuously adjusted to maintain constant scaling power. The foot switch device is connected to a boost enabler in the base unit by a connector cable. The foot switch can include first and second electrical contact positions, where the second position provides a temporary boost in power to the handpiece.

Beerstecher, U.S. Pat. No. 6,866,507 discloses a foot switch device for controlling the operation of a dental apparatus having a multifunctional handpiece. The foot switch device includes a base plate and a relatively movable cover plate. A space between the base plate and cover plate forms a fluid tight hollow cavity. Multiple press switches are arranged in the hollow cavity. The press switches are made from a printed circuitry, which is sandwiched between first and second carrier foils. A signaling line connects the foot switch device to the electronic control systems of the dental apparatus.

Feine, U.S. Pat. No. 6,893,261 discloses a foot switch for controlling an ultrasonic dental scaler. The foot switch incorporates the circuitry for controlling the vibrational frequency of the scaling insert and can also provide water and light to a remote head unit. A cable bundle connects the foot switch to the remote head. The foot switch housing is connected to a power supply and is additionally connected to a water source. The foot switch housing can also include a light source such as an argon lamp. The remote head can be attached to a dental treatment chair or it may be carried on the belt of a dentist or dental hygienist.

Conventional foot switches are generally effective; however, there is a need for an improved foot switch device. For example, some conventional foot switches have a relatively high, pointed cover that is mounted over the foot switch base. Consequently, an operator may feel an uncomfortable sensation while pressing the cover with his or her foot. It thus would be desirable to have a foot switch that includes a relatively flat cover with a comfortable foot-engaging surface. The foot switch should be durable and lightweight. The foot switch should also have good dimensional stability so that it cannot be tipped over easily. Furthermore, the foot switch should be capable of being activated by depressing the upper cover at any point along its perimeter. In other words, the foot switch should have a full three hundred and sixty-degree (360°) level of perimeter activation. Additionally, it would be desirable to have a foot switch that could be used to activate a dental/medical unit in a hard-wired or wireless system. The present invention provides such a foot switch having these objects, features, and advantages as well as others.

SUMMARY OF THE INVENTION

The present invention relates to a foot switch device used for activating a dental or medical treatment apparatus. The foot switch device includes a base plate for supporting the foot switch device on the floor; a central housing attached to the base plate, an upper cover mounted on the housing, and a connecting collar attached to the upper cover for retaining the cover on the housing while allowing the cover to move upwardly and downwardly relative to the housing. The central housing contains a first electrical switch for transmitting a first signal to the apparatus, a second electrical switch for transmitting a second signal to the apparatus, and an actuator assembly for activating the switches. The actuator assembly includes (i) an actuating plunger capable of moving in upward and downward directions, (ii) a first switch activator tab, and (iii) a second switch activator tab. An operator depresses the upper cover with his or her foot so that the cover engages the actuating plunger. As force is applied to the plunger, the plunger moves downwardly to a first position, where it engages the first switch activator tab, thereby causing the first switch to be activated. A second force applied to the plunger causes the plunger to move downwardly to a second position, where it engages a second switch activator tab, thereby causing the second switch to be activated.

The foot switch device is preferably used to control the operation of a dental treatment apparatus and more preferably an ultrasonic dental scaler. The foot switch can be used to control the operation of an ultrasonic dental scaler in a wireless, remote control system or in a hard-wired system. Activating the first switch in the foot switch device causes the dental scaler unit to run in a first mode of operation and activating the second switch causes the unit to run in a second mode. For example, the first mode of operation can be normal ultrasonic scaling power, and the second mode can be boosted ultrasonic scaling power.

BRIEF DESCRIPTION OF THE DRAWINGS

The novel features that are characteristic of the present invention are set forth in the appended claims. However, the preferred embodiments of the invention, together with further objects and attendant advantages, are best understood by reference to the following detailed description in connection with the accompanying drawings in which:

DETAILED DESCRIPTION OF THE PREFERRED EMBODIMENTS

Figure 1:
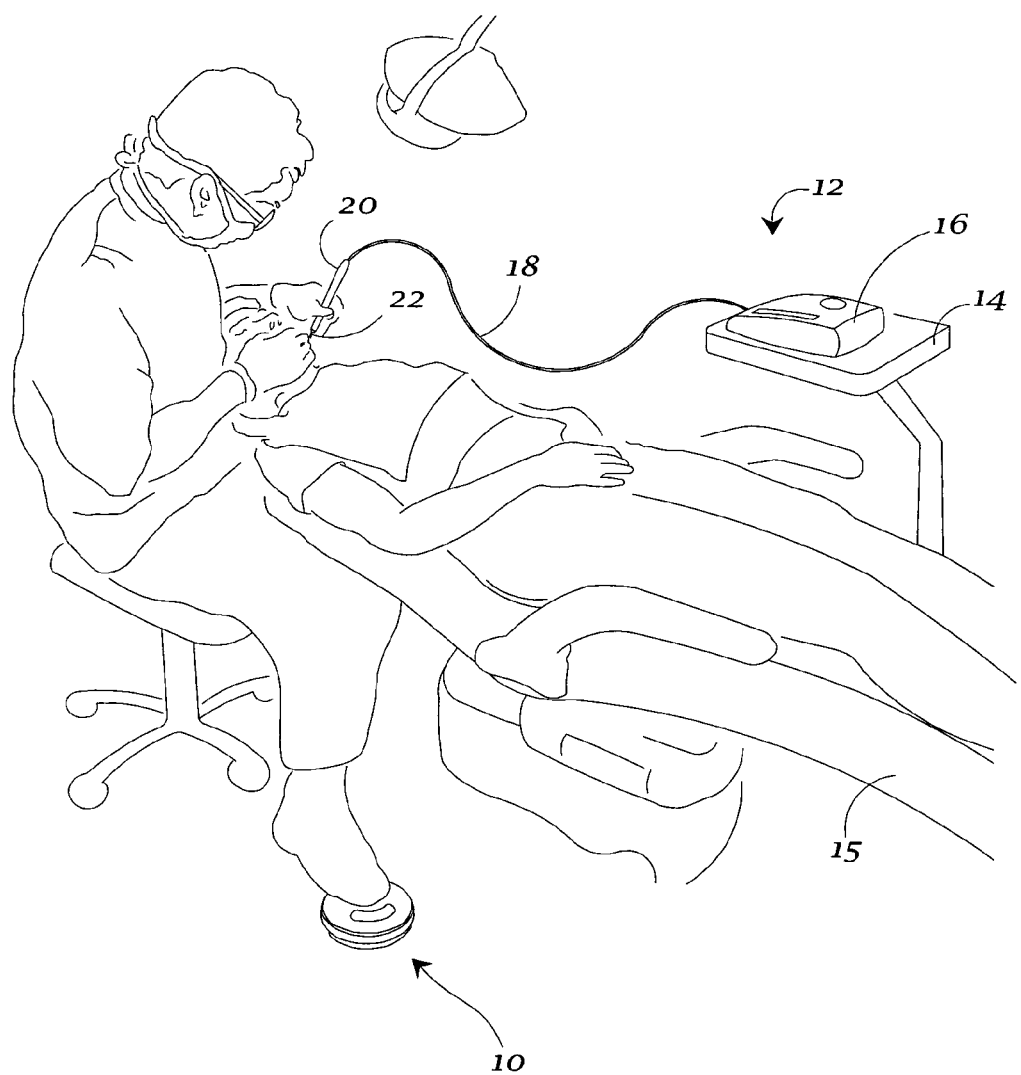
FIG. 1 is a perspective view of the foot switch device of the present invention showing a dental professional using the device to control the operation of an ultrasonic dental scaler in a remote, wireless system.

Referring to the drawings, FIG. 1 illustrates one embodiment of the foot switch device (10) of the present invention. In FIG. 1, a dental professional is shown pressing the foot switch device (10) in order to activate a dental treatment apparatus, particularly an ultrasonic dental scaler unit (12), which is seated on a tray (14) attached to a dental chair (15). Dental professionals use ultrasonic dental scalers (12) to provide therapeutic and preventive care to their patients. The ultrasonic scaler (12) is used primarily to remove calculus deposits and plaque from tooth surfaces. The ultrasonic dental scaler (12) includes a base power unit (16). A flexible and lightweight cable (18) connects a handpiece (20) to the base unit (16). A power scaling insert (22) is inserted into the handpiece (20). Different scaling inserts (22) are used depending upon the health of the patient, the tooth to be treated, and the type of deposits to be removed. The scaling insert (22) is based on magnetostrictive or piezoelectric technology and vibrates at an ultrasonic frequency to remove deposits from tooth surfaces.

In essence, both magnetostrictive and piezoelectric systems convert electric signals into mechanical motion of the scaling insert (22), but they use different mechanisms to do so. In a piezoelectric system, fixed ceramic crystals in the handpiece (20) vibrate to cause the tip of the scaling insert (22) to move in a linear stroke pattern. In a magnetostrictive system, the handpiece (20) includes an energizing coil that surrounds the scaling insert (22). The scaling insert (22) comprises a transducer that is formed from a stack of laminar plates made of magnetostrictive material. The energizing coil excites the plates of magnetostrictive material via a magnetic field so that the plates longitudinally expand and contract at ultrasonic frequencies. This causes the tip of the scaling insert (22) to vibrate in an elliptical stroke pattern. The tip of the scaling insert (22) vibrates at an ultrasonic frequency, which is defined generally as being within the range of 18 to 50 kHz (18,000 to 50,000 cycles per second). It is common for the scaling insert (22) to have an operational frequency of either 25 kHz or 30 kHz. Although the foot switch device (10) will be described herein as controlling an ultrasonic dental scaler (12) primarily, it should be understood that the foot switch device (10) can be used to control the operation of any medical or dental treatment apparatus.

For example, the foot switch device (10) of this invention may be used to control the operation of electrocardiogram machines, X-ray machines, surgical cutting instruments, endoscopic and laproscopic tools, blood analyzers, diagnostic tools, dental chairs, dental irrigators, dental air polishing and prophylaxis systems, dental drills, endodontic and periodontic handpieces, and other dental equipment. The foot switch device (10) is shown in FIG. 1 as controlling the operation of an ultrasonic dental scaler (12) for illustration purposes only, and FIG. 1 should not be construed as limiting the scope of the invention.

As shown in FIG. 1, the foot switch device (10) is preferably used to operate a dental/medical treatment apparatus (12) in a wireless, remote control system. In such a system, the foot switch (10) may include a transmitter that transmits a radio frequency (RF) signal to a RF receiver in the base unit (16) of the dental/medical apparatus (12), which receives the signal. When the RF receiver in the base unit (16) receives the RF signal, it activates the base unit (16) and the handpiece (20) (or other instrument) that is attached to the unit (16). The RF transmitter and receiver can be replaced with RF transceivers if desired. The RF transceiver is capable of both transmitting and receiving RF signals. Wireless information including, for example, identification codes, equipment status, alarm messages, and the like may be sent back and forth between the foot switch device (10) and dental/medical apparatus (12) using the RF transceivers according to this embodiment of the invention. It is recognized that wireless communication systems, other than RF systems, could be used. For example, infrared or ultrasound communication systems could be used.

Alternatively, the foot switch device (10) of this invention may be used to operate the dental/medical apparatus (12) in a hard-wired system. In such a system, the foot switch device (10) is connected to the base unit (16) by a connector cable (not shown in FIG. 1) extending from the device (10). The foot switch device (10) is tethered to the base unit (16) in this manner. The switching signals are sent from the foot switch device (10) to the base unit (16) via the connector cable.

One advantageous feature of the foot switch device (10) of this invention is that it can be used in either wireless or hard-wired systems. An auxiliary connector cable can be provided with the foot switch (10) and this cable can be installed to tether the foot switch (10) to the base unit (16) in the event that the foot switch (10) is unable to communicate with the base unit (16) via the RF signals. For example, if the battery power in the foot switch (10) is too low, the auxiliary connector cable can be installed to connect the foot switch (10) to the base unit (16). Such wireless and hard-wired systems are described in co-pending and co-assigned patent application entitled "Hard-Wired and Wireless System with Footswitch for Operating a Dental or Medical Treatment Apparatus," the disclosure of which is hereby incorporated by reference.

Figure 2:
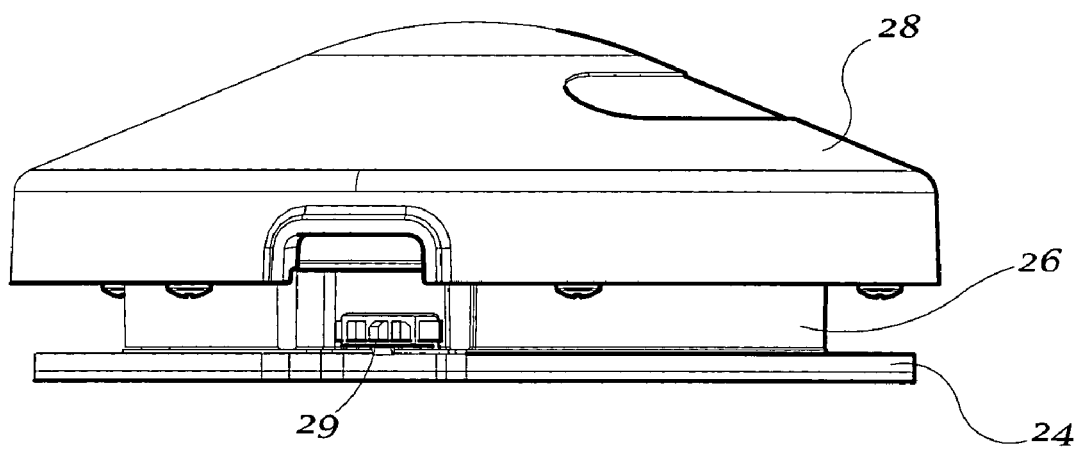
FIG. 2 is a close-up side perspective view of the foot switch device.

Referring to FIG. 2, a side perspective view of the foot switch device (10) of this invention is shown. The foot switch (10) generally includes a base plate (24), a central body or housing (26), and an upper, moveable cover (28). An auxiliary connector (29) is provided for attaching a connector cable so that the foot switch device (10) can be connected to the base unit of the dental/medical treatment apparatus.

Figure 3:
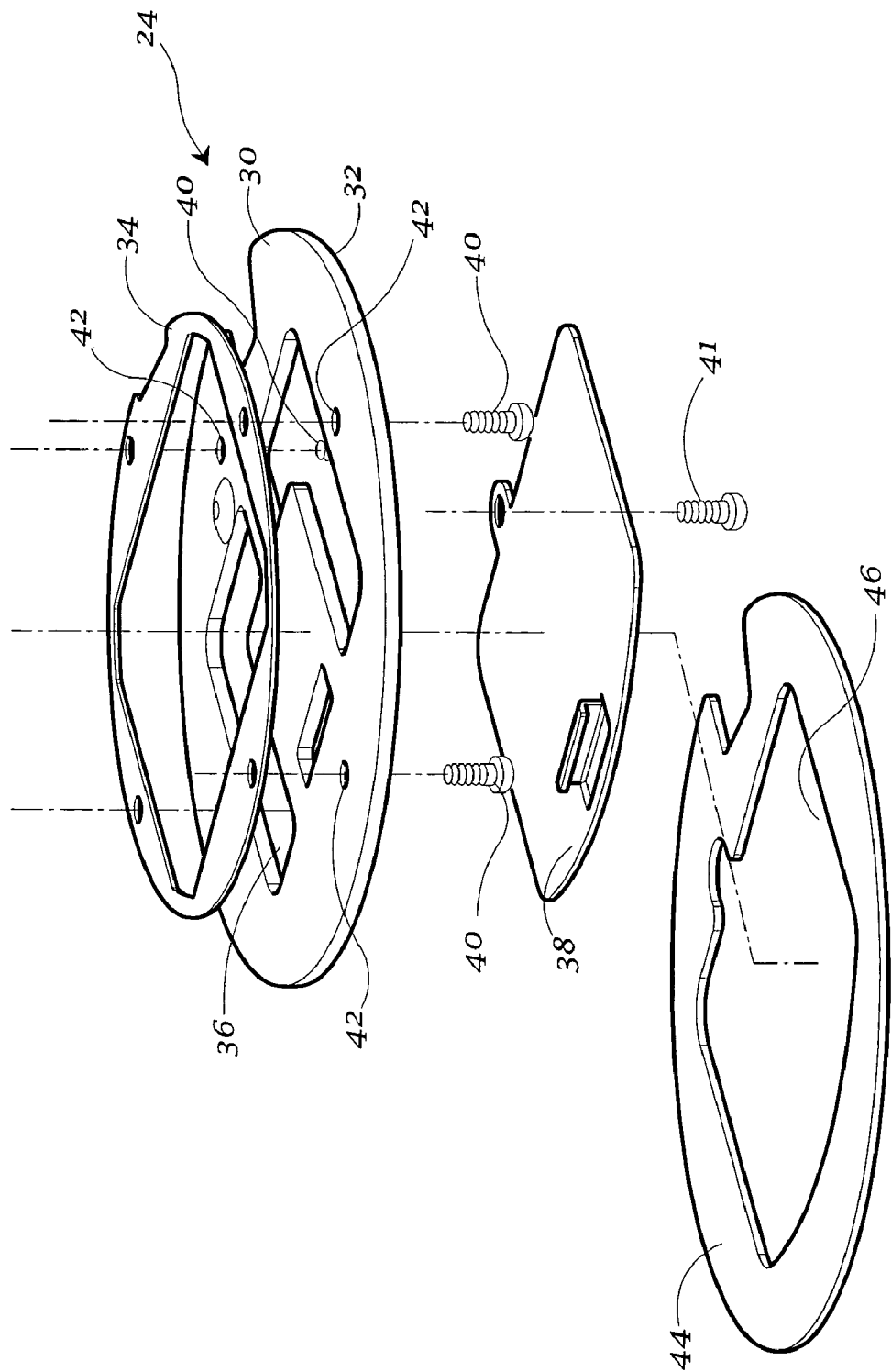
FIG. 3 is an exploded view of the sealing gasket, base plate, battery door, and non-skid backing of the foot switch device.

In FIG. 3, an exploded view of the base plate (24) is shown. The base plate (24) has a generally circular structure and includes an inner (top) surface (30) and outer (bottom) surface (32). A sealing gasket (34) is mounted to the top surface (30). The base plate (24) further includes a battery compartment access opening (36) that is enclosed by a battery door (38). Standard batteries can be installed to supply power to the foot switch device (10). As discussed above and shown in FIG. 1, the foot switch device (10) is preferably used to control the dental/medical apparatus (12) in a remote, wireless system. Alternatively, the foot switch (10) can be used in a hard-wired system, wherein a connector cable is used to tether the foot switch (10) to the base unit (16). In such instances, the connector cable is attached so that it runs from the auxiliary connector (29) (FIG. 2) of the foot switch device (10) to the base unit (16). In FIG. 3, the base plate (24) is attached to the central housing (not shown) by screws or other fasteners (40) that are inserted through screw holes (42). The battery door (38) is secured to base plate (24) by battery door screw (41). The bottom surface (32) of the base plate (24) can be outfitted with a non-skid, rubber backing (44) to help keep the foot switch device (10) in place on the floor. The non-skid backing (44) may contain a cut-out portion (46) so that a person may easily access the battery door (38).

Figure 4:
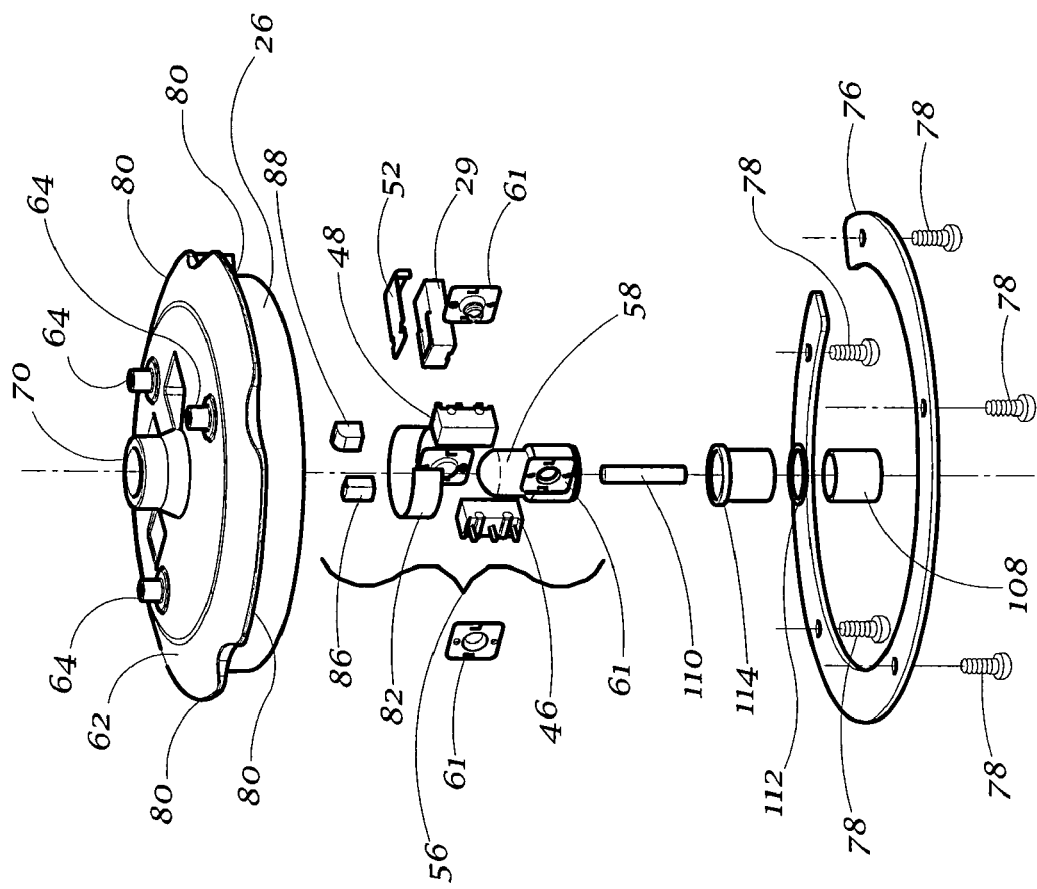
FIG. 4 is an exploded view of the central housing, actuating assembly, and connecting collar of the foot switch device.
Figure 5:
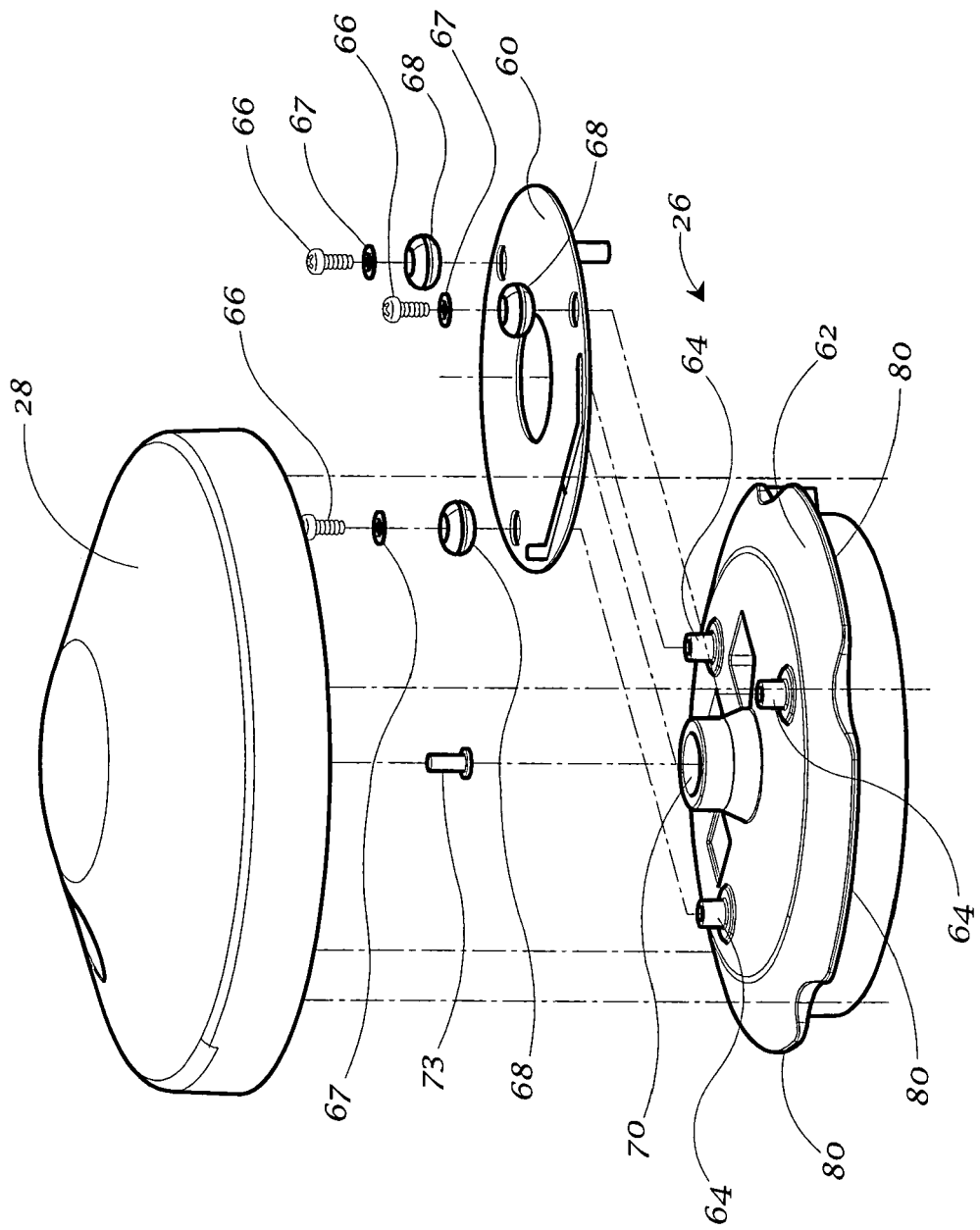
FIG. 5 is an exploded view of the upper cover member, printed circuit board, and central housing of the foot switch device.
Figure 6:
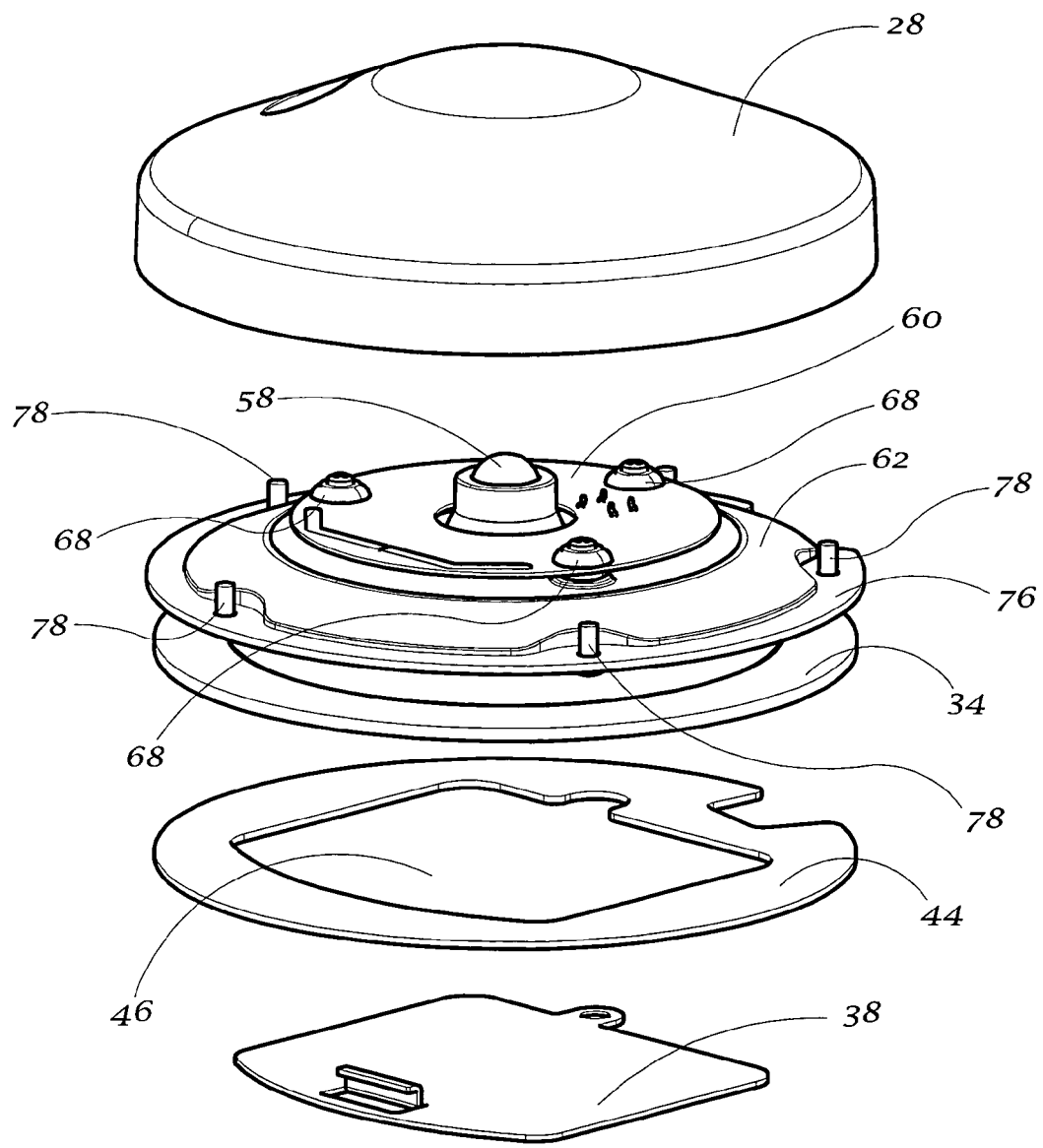
FIG. 6 is an exploded view of the complete foot switch device including the battery door, base plate, central housing, and upper cover member.
Figure 7:
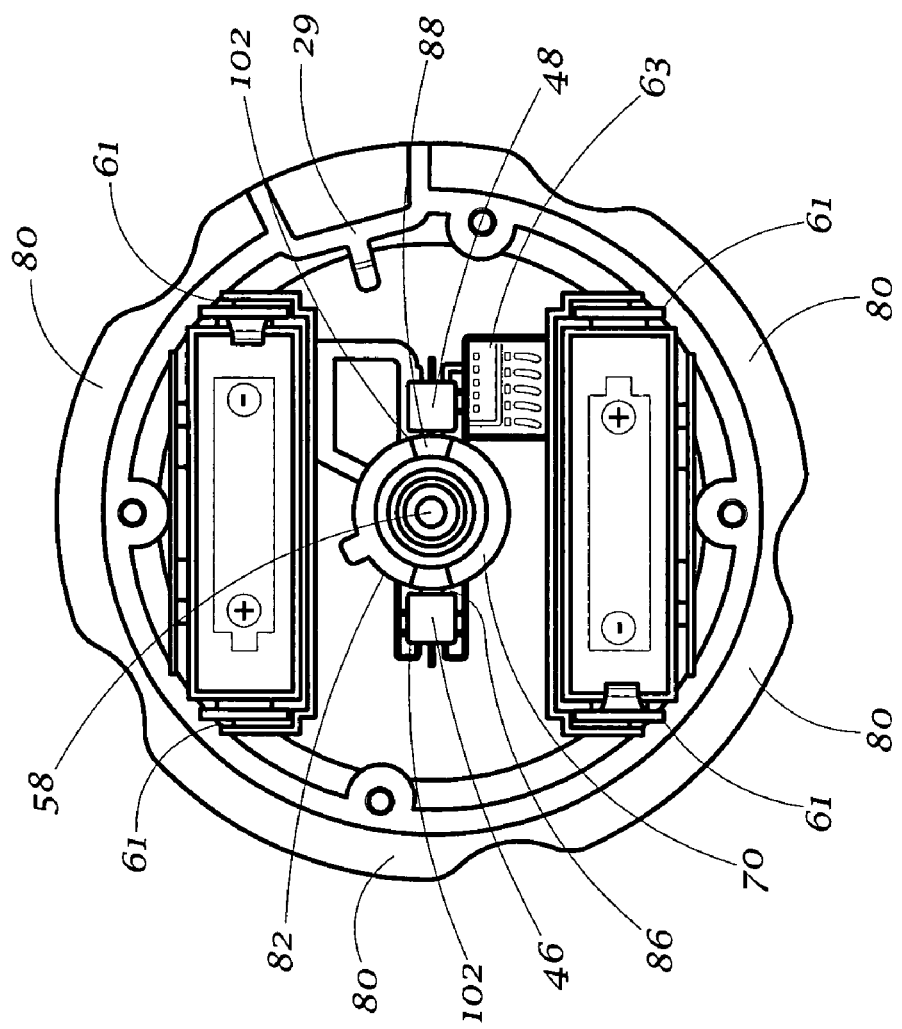
FIG. 7 is a bottom perspective view of the foot switch device showing the plunger throughbore, first activator switch, and second activator switch, wherein the base plate has been removed.

The central housing (26), which is shown in the exploded views of FIGS. 4-6, is fastened to the base plate (24). Referring to FIG. 4, the housing (26) contains a first electrical switch (46) for transmitting a first electrical signal to the dental/medical treatment apparatus (12), and a second electrical switch (48) for transmitting a second signal to the dental/medical treatment apparatus (12). The switching mechanism also includes a wiring harness generally indicated at (50). The wiring harness (50) includes auxiliary connector (29), first and second switches (46, 48), battery terminals (61) (FIG. 7), and wiring. The wiring harness is connected to the circuit board (60) through a circuit board connector (63) that is shown in FIG. 7. In FIG. 4, an auxiliary connector curtain (52) is shown being used to protect the auxiliary connector (29). The connector curtain (52) is a rubber shroud material that is draped over the auxiliary connector (29) to prevent the ingress of fluid, for example, mop water, which is used to clean the floor where the foot switch device (10) rests. The connector curtain (52) is an optional element, which may be installed as needed. In other embodiments of the foot switch device (10), a connector curtain (52) is not used. The central housing (26) further contains an actuator assembly generally designated at (56), which includes a vertical plunger (58), for activating the first and second switches (46, 48). The switch-activating mechanism is discussed in further detail below.

Referring to FIG. 5, a printed circuit board (60) is mounted on the upper surface (62) of the central housing (26). The upper surface (62) includes hollow post members (64) extending therefrom. The printed circuit board (60) is secured to the upper surface (62) by mounting screws (66) that are inserted into the hollow post members (64). As shown in FIG. 5, the mounting screws (66) are first passed through washers (67) and rubber grommets (68). The printed circuit board (60) includes a microcontroller for generating appropriate command signals that will be sent to the dental/medical apparatus (12) upon activation of the foot switch (10) and for performing other programmable functions as needed.

In FIG. 6, the circuit board (60) is shown in a mechanically isolated position. Referring to FIG. 7, the circuit board (60) is considered to be isolated, because the battery terminals (61) are connected to the board (60) through a circuit board connector (63). Wire leads (not shown) run from the battery terminals (61) to the connector (63), which connects the wire leads to the circuit board (60). The wire leads can flex to absorb mechanical forces that are applied to the foot switch device (10). The wire leads help prevent such forces from cracking solder joints and causing other damage to the circuit board (60). For example, if the foot switch device (10) is accidentally dropped, the wire leads will help absorb the force of impact to the circuit board (60). A plunger through-bore (70) extends upwardly from the upper surface (62) of the central housing (26). The plunger through-bore (70) is adapted for receiving the vertical plunger (58), which is used to activate the first and second switches (46, 48) located within the central housing (26).

Figure 8:
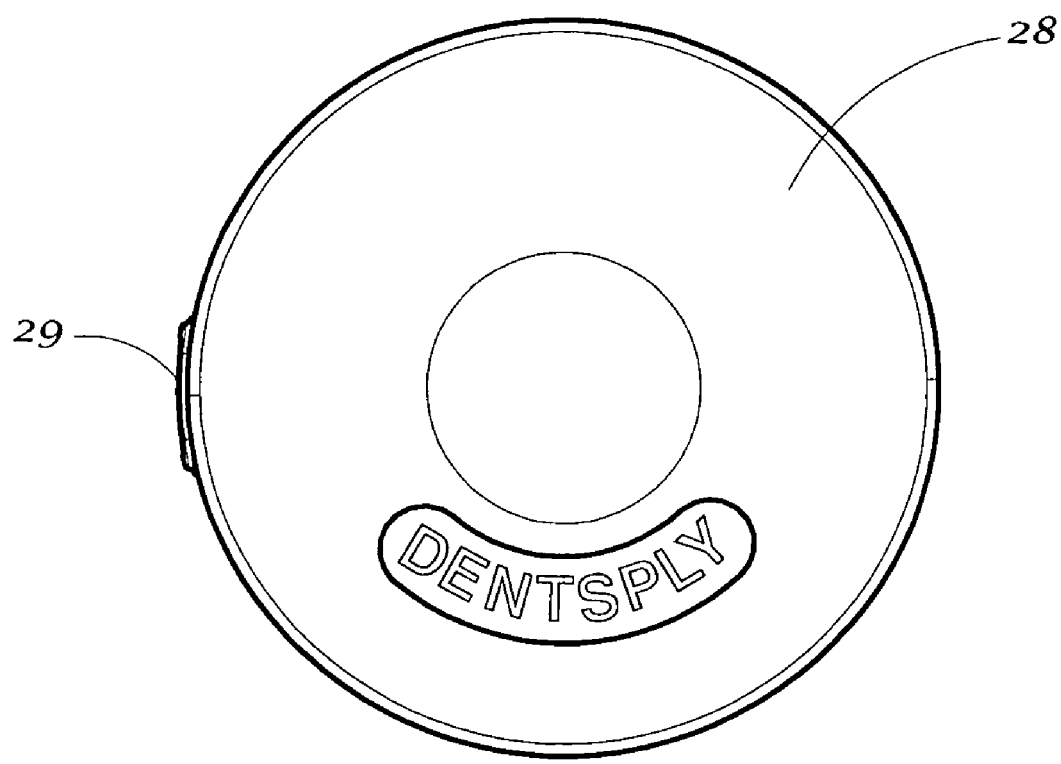
FIG. 8 is a top perspective view of the foot switch device showing the upper, moveable cover.
Figure 11:
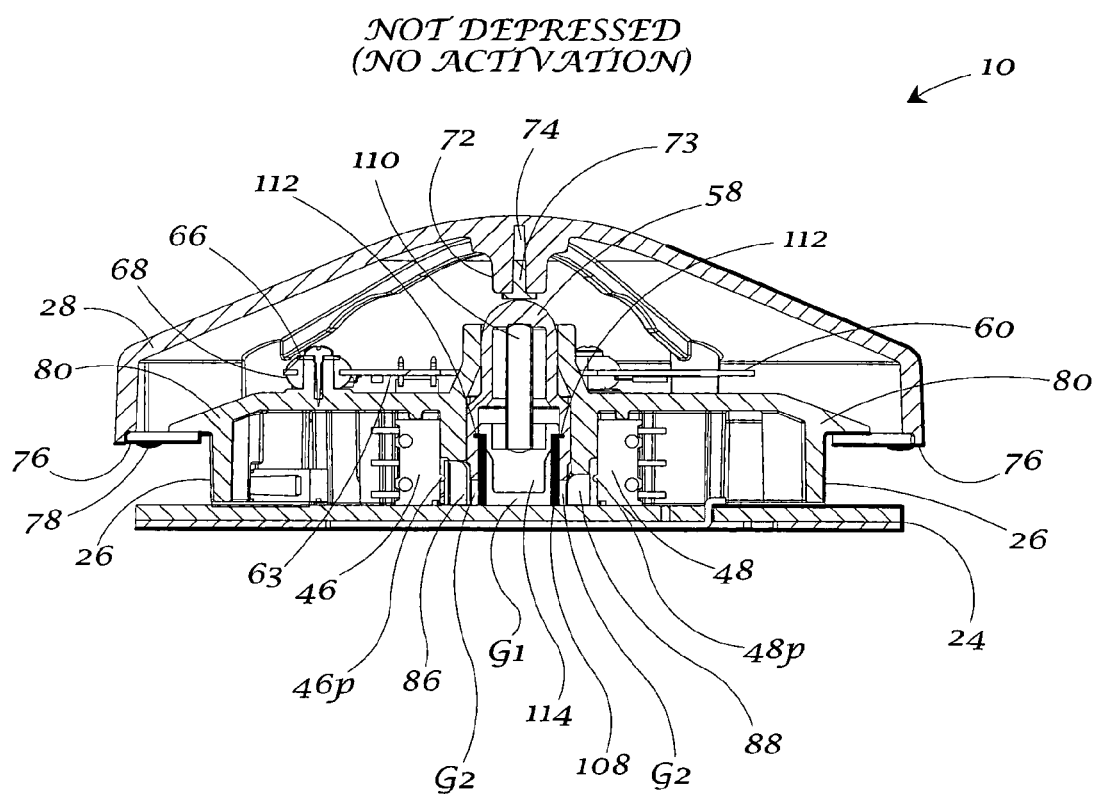
FIG. 11 is a cross-sectional view of the foot switch device showing the device in an initial, non-activated position.
Figure 12:
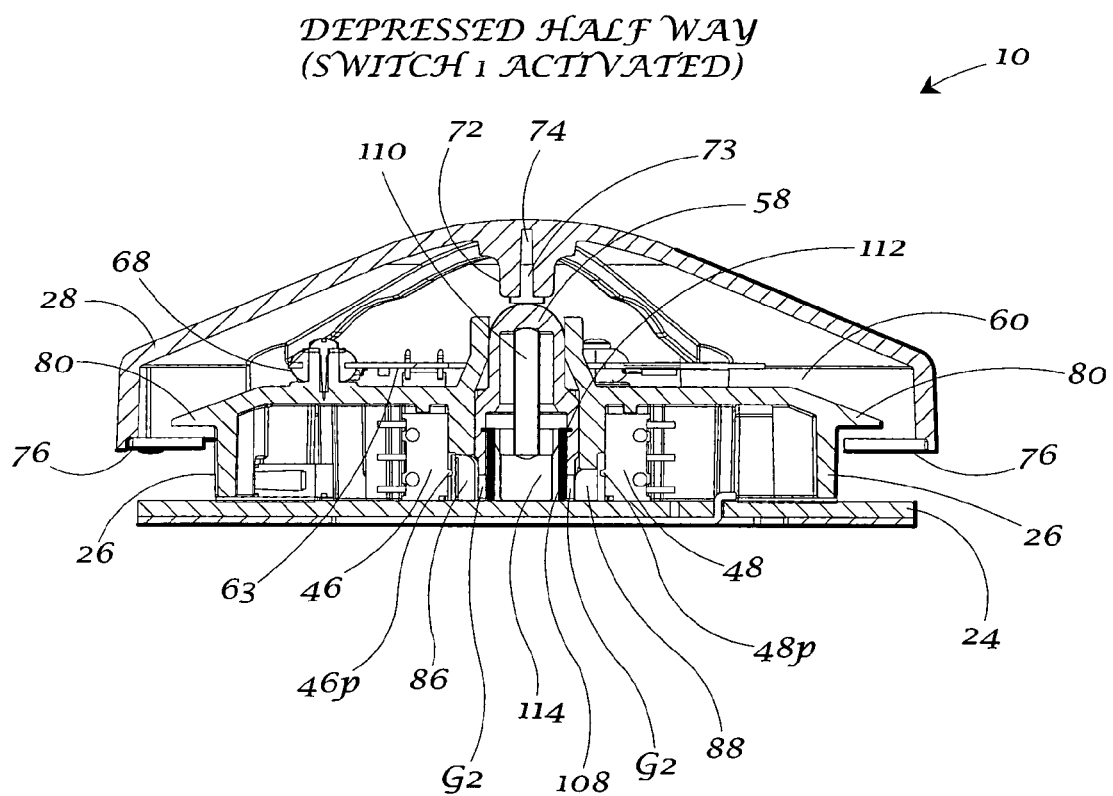
FIG. 12 is a cross-sectional view of the foot switch device showing the first activator switch in an activated position.
Figure 13:
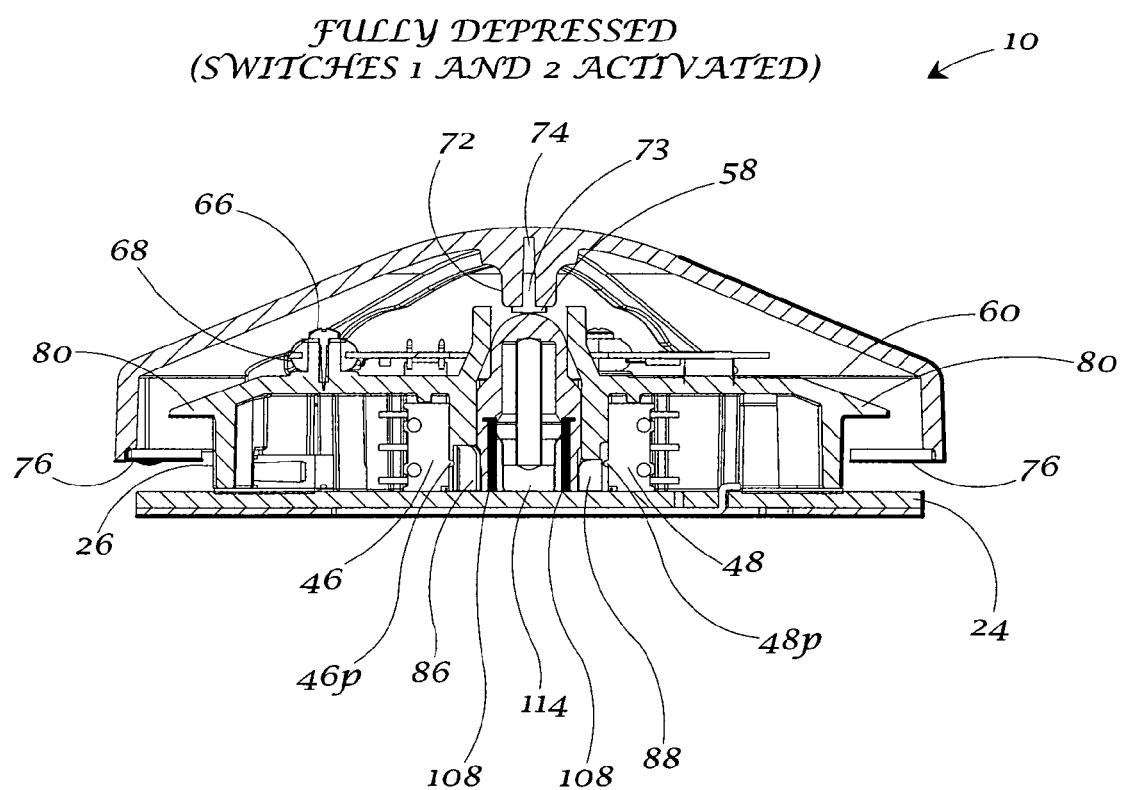
FIG. 13 is a cross-sectional view of the foot switch device showing the second activator switch in an activated position.

In FIG. 8, a top perspective view of the foot switch device (10) is shown. The upper cover (28) has a generally round, dome-like structure which is mounted over and around the central housing (26). The upper cover (28) is mounted over the housing (26) so as to form a hollow cavity within the upper portion of the foot switch device (10). The upper cover (28) is moveable relative to the housing (26) as described further below. The upper cover (28) includes an elongated, inner cover member (72) for engaging the actuating plunger (58) as shown in FIGS. 11-13. The inner cover member (72) extends downwardly from the inner surface of the upper cover (28). The inner cover member (72) may include a headed spirol pin (73), which is inserted into a pin-receiving boss (74) integrally molded to the inside surface of the upper cover (28).

In FIGS. 4-6, the foot switch device (10) also includes a connecting collar (76) having a generally C-shaped or split-ring structure. While a C-shaped connecting collar (76) is preferred, it is recognized that the collar (76) can have other structures. For example, the connecting collar (76) can have a fully circular ring structure so that it completely surrounds the upper cover (28). As shown in FIGS. 11-13, the connecting collar (76) is attached to the upper cover (28). The connecting collar (76) may be secured to the upper cover (28) by screws, bolts, or other suitable fasteners (78). The screws (78) are inserted into hollow post members (not shown) extending from the inside surface of the upper cover (28). The connecting collar (76) helps retain the upper cover (28) on the central housing (26), while allowing the cover (28) to move upwardly and downwardly relative to the housing (26). As further shown in FIGS. 11-13, the central housing includes flange members (80) that radiate outwardly and overlap at least a portion of the connecting collar (76). The radiating flange members (80) and connecting collar (76) cooperate with each other to allow for upward and downward movement of the upper cover (28) relative to the central housing (26) as described further below.

The actuating assembly (56), which is enclosed within the central housing (26), is used to activate the first and second electrical switches (46, 48). The actuating assembly (56) includes a central actuating plunger (58) capable of moving in upward and downward directions; a band spring (82); a first switch activator tab (86); and a second switch activator tab (88). It is recognized that the band spring (82) could include projecting first and second switch activating elements (not shown) that function in a manner similar to the first and second switch activator tabs (86, 88).

Figure 9:
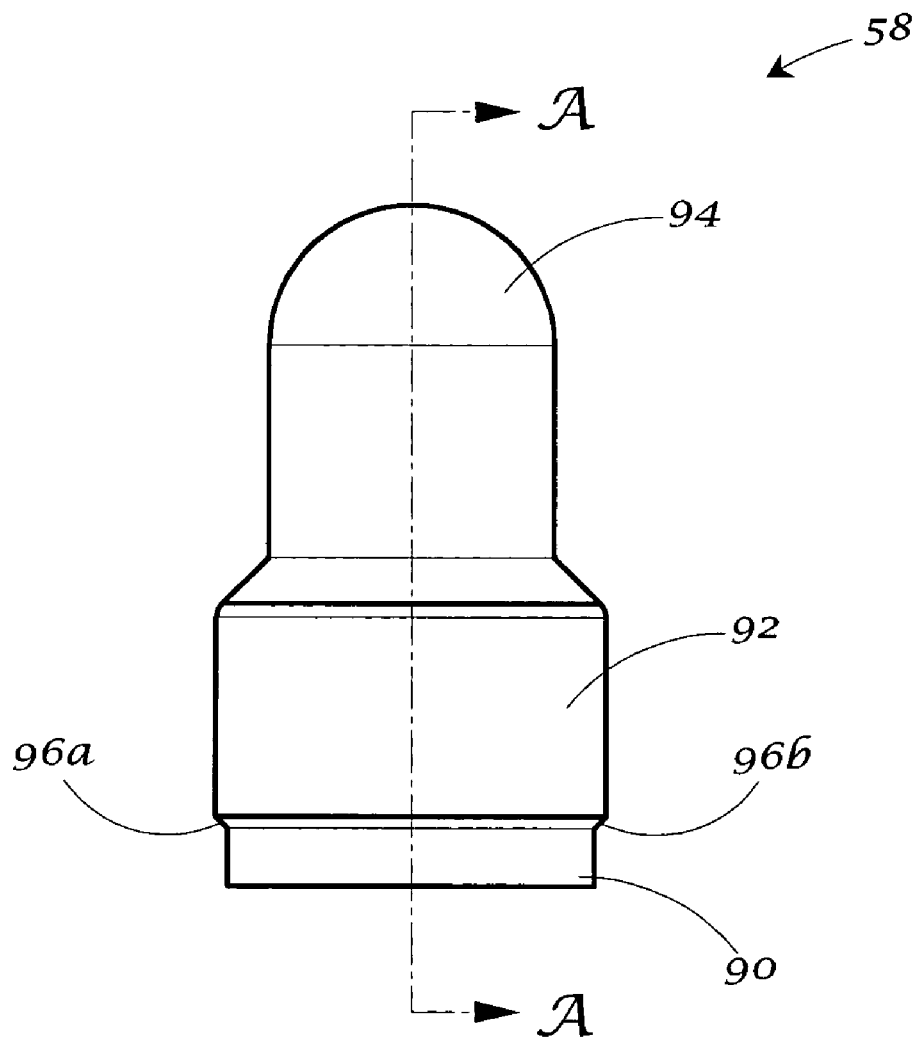
FIG. 9 is a close-up perspective view of the vertically actuating plunger.
Figure 9A:
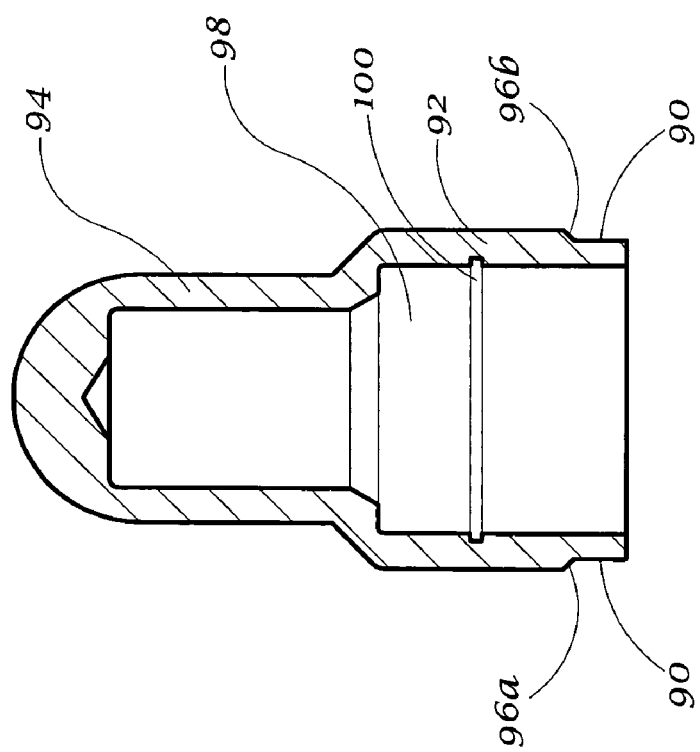
FIG. 9A is a cross-sectional view of the actuating plunger along Line A-A of FIG. 9.

In FIGS. 9 and 9A, a close-up view of the vertically actuating plunger (58) is shown. The actuating plunger (58) is a unitary structure including a base portion (90), a central actuating portion (92), and an upper piloting portion (94). As shown in FIGS. 9 and 9A, the outside diameter of the base portion (90), or primary outside diameter, is relatively small, while the outside diameter of the central actuating portion (92), or secondary outside diameter, is relatively large. The primary and secondary outside diameters of the actuating plunger (58) may be any suitable size and will vary depending upon the dimensions and geometry of the foot switch device (10). The actuating plunger (58) includes integrally shaped ramp or sloping segments (96a, 96b) that adjoin the base (90) to the central actuating portion (92). The ramp segments (96a, 96b) are disposed at an angle of about forty-five-degree (45°). It is preferred that the ramp segments (96a, 96b) be disposed at a forty-five degree (45°) angle. But, it is recognized that the ramp segments (96a, 96b) of the actuating plunger (58) can be positioned at any suitable angle so long as they can interfittingly mate with the angular segments (106a, 106b) of the switch activator tabs (86, 88) as discussed in further detail below. For example, the ramp segments (96a, 96b) of the actuating plunger (58) can be disposed at a thirty-degree (30°) or sixty-degree (60°) angle if desired. As shown in FIG. 9A, the actuating plunger (58) includes a hollow inner cavity (98) adapted for receiving a spring assembly (not shown), which is described further below. The spring assembly includes a retaining ring (112) (FIG. 4), which fits in a retaining ring groove (100) (FIG. 9A) located within the inner cavity (98) of the plunger (58).

Figures 10, 10A:
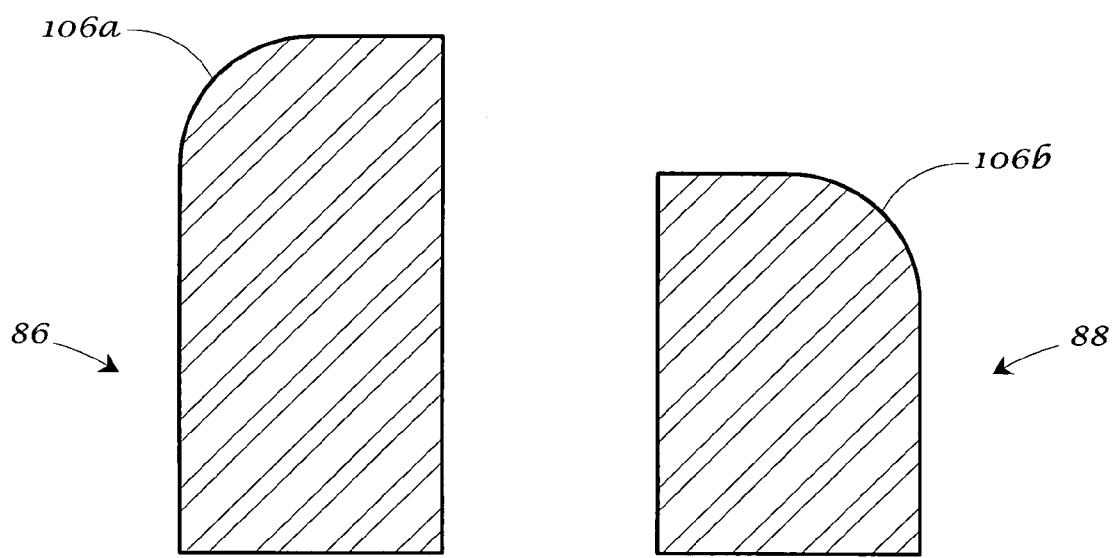
FIG. 10 is a close-up side perspective view of the first activator tab.
FIG. 10A is a close-up side perspective view of the second activator tab.

In FIGS. 10 and 10A, close-up views of the first and second switch activator tabs (86, 88) are shown. The first and second switch activator tabs (86, 88) have different dimensions, which allow them to be activated at different points in the operation cycle of the foot switch device (10). In the embodiment shown in FIGS. 10 and 10A, the first switch activator tab (86) has a relatively long length, while the second switch activator tab (88) has a relatively short length. In addition, the first and second switch activator tabs (86, 88) each include a sloping segment (106a, 106b) for engaging the complementary-shaped sloping segments (96a, 96b) of the actuating plunger (58). A band spring (82) surrounds the plunger through-bore (70) and forces the first and second switch activator tabs (86, 88) inwardly (FIG. 4). The plunger through-bore (70) includes recessed pockets (102) in its peripheral wall for receiving the first and second switch activator tabs (86, 88) (FIG. 7). The first and second switch activator tabs (86, 88) are located opposite to each other. It should be recognized that the relative dimensions of the first and second switch activator tabs (86, 88) shown in FIGS. 10 and 10A are for illustration purposes only. The first and second switch activator tabs (86, 88) can be of any relative length, provided however, that the activator tabs (86, 88) have differing lengths.

The depression of the upper cover member (28) to activate the first and second electrical switches (46, 48) located within the central housing (28) now will be described with reference to FIGS. 11-13.

Referring first to FIG. 11, the foot switch device (10) is initially in a non-activated state with the actuating plunger (58) in a fully extended, non-depressed position. Particularly, the vertically moveable plunger (58) is shown extending upwardly through the plunger through-bore (70). At this point, the first and second switch activator tabs (86, 88) are spring-biased inwardly against the base portion (90) of the plunger (58) by the band spring (82). Also, as shown in FIG. 11, the radiating side flange members (80) of the central housing (26) are engaged with the edge portions of the surrounding connecting collar (76).

To activate the foot switch device (10), the operator depresses the upper cover (28) with his or her foot using sufficient pressure to cause the inner cap member (72) to move downwardly and engage the actuating plunger (58). One advantageous feature of the foot switch device (10) of this invention is that the operator may depress any region of the upper cover (28) in order to activate the switching mechanism. For instance, the operator may depress the central region of the upper cover (28) to activate the switching mechanism. Alternatively, the operator may activate the foot switch (10) by simply depressing a point along the outer perimeter of the upper cover (28). The device has a three hundred and sixty-degree (360°) level of perimeter activation. In other words, an operator may activate the foot switch (10) by depressing the upper cover (28) at any point along its perimeter.

Turning next to FIG. 12, the operator has depressed the upper cover member (28), thereby forcing the actuating plunger (58) to move downwardly and activating the first electrical switch (46). As shown in FIG. 12, the radiating flange members (80) of the central housing (26) are now disengaged from the edge portions of the connecting collar (76). As the actuating plunger (58) is forced to travel downwardly, the first ramp segment (96a) of the plunger (58) inter-fittingly mates with the complementary-shaped sloping segment (106a) of the first switch activator tab (86), which is the longer of the two switch activator tabs (86, 88). The actuating plunger (58) continues to travel downwardly as the ramp segment (96a) of the plunger slides along the sloping segment (106a) of the switch activator tab (86). The central actuating portion (92) of the plunger (58) eventually comes into contact and engages the first switch activator tab (86). At this point, the central actuating portion (92) acts as a cam and forces the switch activator tab (86) to move outwardly. This action forces the surrounding band spring (82) also to move outwardly so that it engages a first microswitch plunger (86p), thereby activating the first switch (46).

Upon activating the first switch (46), the foot switch device (10) is considered to be operating in Stage 1, and the dental handpiece (20) (or other instrument), which is attached to the base unit (16) of the dental/medical apparatus (12), is powered to run in a first operating mode. In a preferred embodiment, Stage 1 is a normal power mode. In other words, normal power is delivered to the dental handpiece (20) when the foot switch (10) is operating in Stage 1. To make the dental handpiece (20) operate in a second mode, the second switch (48) of the foot switch device (10) is activated. In FIG. 13, the second switch (48) has been activated. Upon activating the second switch (48), the foot switch device is considered to be operating in Stage 2, and the handpiece (20) is powered to run in a second mode. In a preferred embodiment, Stage 2 is a boosted power mode. In other words, a boost in power is delivered to the handpiece (20) when the foot switch device (10) is operating in Stage 2.

An operator can make the foot switch device (10) operate in Stage 2 by exerting additional downward pressure upon the upper cover (28). This action causes the plunger (58) to continue moving in a downward direction. As the actuating plunger (58) is forced to travel further downward, the opposing ramp segment (96b) of the plunger (58) inter-fittingly mates with the complementary-shaped sloping segment (106b) of the second switch activator tab (88), which is the shorter of the two switch activator tabs (86, 88). The actuating plunger (58) continues to travel downwardly as the ramp segment (96b) of the plunger (58) slides along the sloping segment (106b) of the switch activator tab (88). The central actuating portion (92) of the plunger (58) eventually comes into contact and engages the second switch activator tab (88). At this point, the actuating portion (92) acts as a cam and forces the switch activator tab (88) to move outwardly. This outward pressure forces the surrounding band spring (82) also to move outwardly so that it engages a second microswitch plunger (48p), thereby activating the second switch (48).

As illustrated in FIG. 4, the actuator assembly (56) further comprises a primary spring (108) and secondary spring (110). The primary spring (108) is captured between a retaining ring (112) in the actuating plunger (58) and the top surface of the base plate (24). The secondary spring (110) is captured within the cavity (98) of the actuating plunger (58) and a secondary spring retainer (114). The compression of the primary and secondary springs (108, 110), as the first and second switches (46,48) are activated, now will be described with reference to FIGS. 11-13.

First, as previously described and shown in FIG. 11, the actuating plunger (58) is initially in a resting, non-depressed position. At this point, there is a small air gap (G1) between the secondary spring retainer (114) and base plate (24), and a small air gap (G2) between the base portion (90) of the actuating plunger (58) and base plate (24) as also shown in FIG. 11. The primary spring (108) exerts a slight upward biasing force on the actuating plunger (58), while the plunger (58) is in this initial resting position, thereby causing the plunger (58) to be in contact with the inner cover member (72).

Referring next to FIG. 12, the dental practitioner or other operator presses the upper cover (28) downwardly, and the inner cap member (72) moves downwardly to engage the plunger (58). When the operator depresses the upper cover (28) and causes the plunger (58) to move in a downward direction, the primary spring (108) is compressed and the secondary spring (110) moves downwardly. The secondary spring (110) is not compressed at this point. As shown in FIG.

12, when the plunger (58) reaches a first, pre-determined, fixed position in its movement downward, the secondary spring retainer (114) bottoms out on the base plate (24). At this point, there is no longer an air gap (G1) between the secondary spring retainer (114) and base plate (24). However, there is still a small air gap (G2) between the base portion (90) of the actuating plunger (58) and base plate (24). The distance that the actuating plunger (58) travels from its initial resting position (FIG. 11) to the first position (FIG. 12) may be any suitable distance and will depend upon the dimensions and geometry of the foot switch device (10). For example, in one embodiment, the plunger (58) travels a distance of about 0.075 inches to reach the first position. It should be understood, of course, that this travel distance represents only one exemplary embodiment. The distance of travel for the plunger (58) may vary. As discussed above, the movement of the actuating plunger (58) to the first position causes the first switch (46) to be activated and the foot switch device (10) now is considered to be operating in Stage 1. When the actuating plunger (58) is in this first position, the primary and secondary springs (108, 110) exert a slight, upward biasing force on the actuating plunger (58).

Now, in FIG. 13, the operator has pressed the upper cover (28) to a further downward position. When the operator exerts additional downward pressure on the upper cover (28), thereby forcing the plunger (58) to continue moving downward, both the primary and secondary springs (108, 110) are compressed as shown in FIG. 13. The actuating plunger (58) moves to a second, predetermined, fixed position. Particularly, the plunger (58) hits the base plate (24) and bottoms out. At this point, there is no longer an air gap (G2) between the base (90) of the actuating plunger (58) and the base plate (24). The distance of travel for the plunger (58) from the first position (FIG. 12) to the second position (FIG. 13) may be any suitable distance. For example, in one embodiment, the plunger (58) travels a distance of about 0.075 inches from the first position to the second position. Thus, the full distance of travel for the plunger (58) would be about 0.150 inches in this embodiment. As noted above, these dimensions are provided only for illustrative purposes and should not be considered restrictive. The actual dimensions may vary and be of any appropriate length. The movement of the actuating plunger (58) to the second fixed position causes the second switch (48) to be activated and the foot switch device (10) is triggered to run in a boosted power mode. When the second switch (48) activates the dental handpiece (20) (or other instrument) to run in a boosted power mode, the foot switch device is considered to be operating in Stage 2.

As discussed above, a sufficient force must be applied to the actuating plunger (58) to cause it to move downward to a first position, thereby activating the first switch (46) and Stage 1. Movement of the plunger (58) to the first position causes the primary spring (108) to be compressed and the secondary spring retainer (114) to bottom out. As additional force is applied and the plunger (58) continues moving downward, both the primary and secondary springs (108, 110) are compressed. A significantly greater force must be applied to the plunger (58) to cause it to move further downward to the second position, thereby activating the second switch (48) and Stage 2. An increase in force is needed to move the plunger (58) from the first position (Stage 1) to the second position (Stage 2), because the secondary spring (110) is pre-loaded by the secondary spring retainer (114) when the plunger (58) is sitting in the first position. As shown in FIG. 12, depressing the plunger (58) to the first position causes the secondary spring retainer (114) to bottom out. Furthermore, the secondary spring (110) has a higher "K factor" meaning that more force is required to compress the secondary spring (110).

Because of the different levels of pressure that must be applied to the upper cover (28), there is a distinct feel between operating the foot switch device (10) in Stage 1 versus Stage 2. Basically, an operator can depress the upper cover (28) until he or she feels the "click" of the secondary spring retainer (114) hitting the base plate (24). At this point, the actuating plunger (58) has reached the first position, thereby activating Stage 1. The foot switch device (10) will continue operating in Stage 1 so long as the operator keeps-up the minimum pressure on the upper cover (28). If the operator wishes to operate the foot switch (10) in Stage 2, he or she must apply additional downward pressure on the upper cover (28). In such an event, the operator continues pressing the upper cover (28) downwardly until he or she feels a second "click" indicating that the actuating plunger (58) has hit the base plate (24) and Stage 2 has been activated. The foot switch device (10) will continue operating in Stage 2 so long as the operator maintains sufficient pressure on the upper cover (28). Since Stage 2 requires a different amount of pressure for activation than Stage 1, the operator can distinctly feel when he or she is entering Stage 2. Also, the operator will realize that he or she must maintain this additional pressure to keep the foot switch device (10) running in Stage 2. After using the footswitch (10) over a sufficient period of time, the operator will get a "feel" as to the amount of force that must be applied to activate Stage 1 versus the force required for activating Stage 2.

Figure 14:
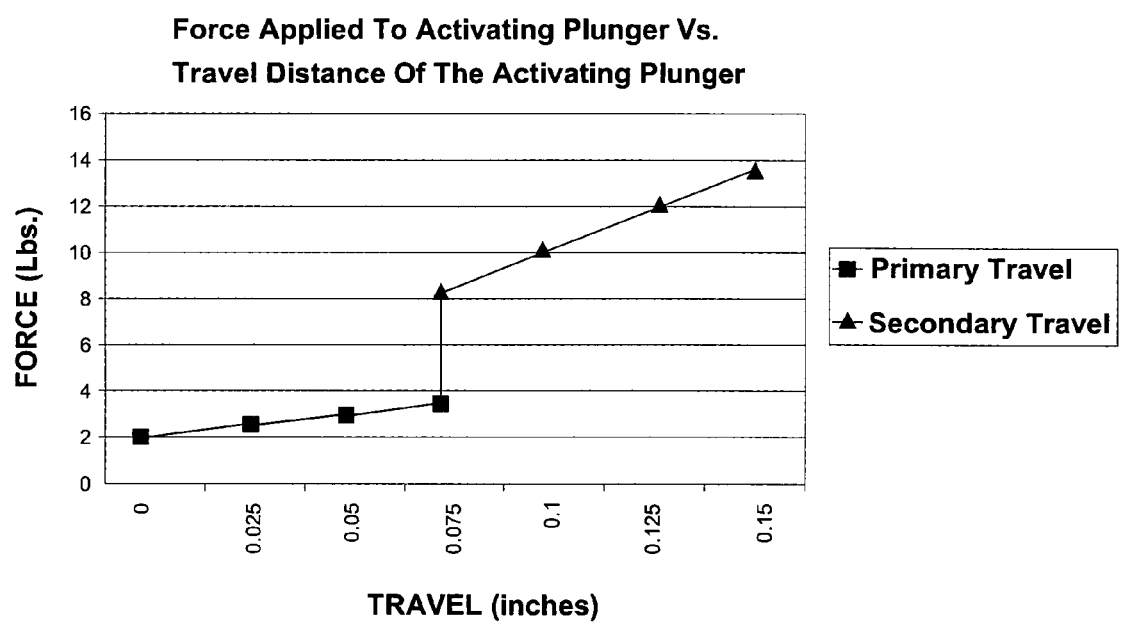
FIG. 14 is a graph showing force applied to the actuating plunger versus travel distance of the actuating plunger.

The difference in actuation force required for entering Stage 1 versus Stage 2 is illustrated in the graph of FIG. 14. As illustrated in FIG. 14, in one embodiment, the actuating plunger (58) travels a distance of 0.075 inches to activate Stage 1, and a gradual increase in force on the upper cover (28) is required to reach this point. Thereafter, a significant increase in force is required to continue depressing the upper cover (28) so that the actuating plunger (58) travels an additional 0.075 inches and activates Stage 2.

The foot switch device (10) of the present invention has many advantageous features. For instance, the round, dome-like upper cover (28) provides a comfortable foot-engaging surface. Additionally, the foot switch (10) is made from a durable polymeric material such as, for example, acetals, acrylics, polyamides, polyesters, polycarbonates, polyolefins, polystyrene, and polyvinyl chloride. The polymeric material may contain reinforcing fillers and other additives. The foot switch has good dimensional stability so that it can rest securely on the surface of the floor and not be tipped over. Moreover, the foot switch (10) has a three hundred and sixty-degree (360°) level of activation so an operator can activate the foot switch by depressing the cover (28) at any point around its perimeter. The foot switch device (10) includes at least two switches, each being activated by depressing the upper cover (28) of the foot switch to a different position. Depressing the cover (28) to a first position closes the first switch (46) and activates Stage 1, and depressing the cover (28) to a second position closes the second switch (48) and activates Stage 2. As a result, the dental/medical apparatus (12) can operate in different modes. For example, activating Stage 1 of the foot switch (10) may cause the dental/medical apparatus (12) to operate in a normal power mode, and activating Stage 2 of the foot switch (10) may cause the dental/medical apparatus (12) to operate in a boosted power mode. Furthermore, the foot switch (10) can be used to activate a dental/medical apparatus (12) in a hard-wired or wireless system.

Workers skilled in the art will appreciate that various modifications can be made to the illustrated embodiments and description herein without departing from the spirit and scope of the present invention. For example, the foot switch device (10) of this invention could contain more than two switches. More particularly, as one example, the foot switch device (10) could contain three switches. Upon activating the first switch, the foot switch would run in Stage 1. Activating the second switch would cause the foot switch to run in Stage 2, and activating the third switch would cause the foot switch to run in Stage 3. In Stage 1, the dental/medical apparatus could operate under normal power. In Stage 2, the dental/medical apparatus could operate under intermediate power, and in Stage 3, the dental/medical apparatus could run under high power.

It is also recognized that the dental/medical apparatus may have different modes of operation, and the foot switch can be used to control these different modes. In other words, the foot switch can be used to activate operational modes other than normal power and boosted power modes. For example, in the case of an ultrasonic dental scaler, the system may be designed for the normal ultrasonic scaling of teeth and for the lavage or medicinal treatment of periodontal pockets below the gumline. In such an example, when Stage 1 is activated, the scaler unit may be designed to run in a normal ultrasonic scaling mode. Then, upon activating Stage 2, the scaler unit may be designed to run simultaneously in an ultrasonic scaling mode and lavage mode. In the lavage mode, antibacterial solutions are dispensed through the scaling insert and into the periodontal pockets. Irrigating the periodontal pockets with these antibacterial solutions may help stop the progression of periodontal disease.

Furthermore, although the foot switch device (10) of this invention has been described herein primarily as being suitable for controlling the operation of a dental or medical apparatus, it should be understood that the foot switch device (10) can be used to operate other any other suitable apparatus. For example, the foot switch device could be used to operate any suitable industrial, occupational, or recreational piece of equipment.

The foregoing are only some examples of modifications that can be made to the illustrated embodiments and description herein without departing from the spirit and scope of the present invention. It is intended that all such modifications within the spirit and scope of the present invention be covered by the appended claims.

What is claimed is:

1. A foot switch device for controlling the operation of a dental or medical treatment apparatus, comprising:
a base plate for supporting the foot switch device on the floor;
a housing attached to the base plate, the housing containing a first electrical switch for transmitting a first signal to the apparatus and a second electrical switch for transmitting a second signal to the apparatus, and an actuator assembly for activating the switches, the actuator assembly comprising: (i) an actuating plunger capable of moving in upward and downward directions, (ii) a first switch activator tab, and (iii) a second switch activator tab, wherein a force applied to the plunger causes the plunger to move downwardly to a first position, where it engages the first switch activator tab, thereby causing the first switch to be activated, and a second force applied to the plunger causes the plunger to move downwardly to a second position where it engages a second switch activator tab, thereby causing the second switch to be activated;
an upper cover mounted on the housing, the cover being moveable relative to the housing, for engaging the actuating plunger; and
a connecting collar attached to the upper cover for retaining the cover on the housing while allowing the cover to move upwardly and downwardly relative to the housing.

2. The foot switch device of claim 1, wherein the foot switch is used to control the operation of a dental treatment apparatus.

3. The foot switch device of claim 2, wherein the dental treatment apparatus is an ultrasonic dental scaler.

4. The foot switch device of claim 1, wherein the foot switch is used to control the operation of an ultrasonic dental scaler in a wireless, remote control system.

5. The foot switch device of claim 1, wherein the foot switch is used to control the operation of an ultrasonic dental scaler in a hard-wired system.

6. The foot switch device of claim 1, wherein activating the first switch causes the ultrasonic dental scaler to run in a first mode of operation.

7. The foot switch device of claim 6, wherein the first mode of operation is normal ultrasonic scaling power.

8. The foot switch device of claim 1, wherein activating the second switch causes the ultrasonic dental scaler to run in a second mode of operation.

9. The foot switch device of claim 8, wherein the second mode of operation is boosted ultrasonic scaling power.

10. The foot switch device of claim 1, wherein the foot switch is used to control the operation of a medical treatment apparatus.

11. The foot switch device of claim 1, wherein the actuating plunger is a unitary structure including a base portion, central actuating portion, and upper piloting portion, the outside diameter of the central actuating portion being greater than the outside diameter of the base portion.

12. The foot switch device of claim 11, wherein the base portion is adjoined to the upper piloting portion by opposing ramp segments, each ramp segment being angled so that it inter-fittingly mates with a complementary-shaped sloping segment of a switch activator tab.

13. The foot switch device of claim 12, wherein each ramp segment is disposed at an angle of about 45 degrees.

14. The foot switch device of claim 1, wherein the first and second switch activator tabs have different dimensions.

15. The foot switch device of claim 14, wherein the first switch activator tab has a length greater than the length of the second switch activator tab.

16. The foot switch device of claim 11, wherein the first and second switch activator tabs each has a sloping segment for engaging the central actuating portion of the actuating plunger.

17. The foot switch device of claim 1, wherein the actuating plunger travels downwardly a distance of about 0.075 inches from an initial, non-depressed position to activate the first switch, and the actuating plunger travels downwardly a distance of about 0.150 inches from an initial, non-depressed position to activate the second switch.

18. The foot switch device of claim 1, wherein the upper cover has a round, dome-like structure.

19. The foot switch device of claim 1, wherein the connecting collar has a split-ring structure.

20. A foot switch device for controlling the operation of a dental or medical treatment apparatus, comprising:
a base plate for supporting the foot switch device on the floor;
a housing attached to the base plate, the housing containing a first electrical switch for transmitting a first signal to the apparatus and a second electrical switch for transmitting a second signal to the apparatus, an actuator assembly for activating the switches, and a spring assembly, the actuator assembly comprising: (i) an actuating plunger capable of moving in upward and downward directions, (ii) a first switch activator tab, and (iii) a second switch activator tab, wherein a force applied to the plunger causes the plunger to move downwardly to a first position, where it engages the first switch activator tab, thereby causing the first switch to be activated, and a second force applied to the plunger causes the plunger to move downwardly to a second position where it engages a second switch activator tab, thereby causing the second switch to be activated; and the spring assembly comprising: (i) a primary spring, and (ii) a secondary spring, wherein the primary spring is compressed as the plunger moves downwardly to a first position and the primary spring and secondary spring are compressed as the plunger moves downwardly to a second position;

an upper cover mounted on the housing, the cover being moveable relative to the housing, for engaging the actuating plunger; and a connecting collar attached to the upper cover for retaining the cover on the housing while allowing the cover to move upwardly and downwardly relative to the housing.

21. The foot switch device of claim 20, wherein the foot switch is used to control the operation of a dental treatment apparatus.

22. The foot switch device of claim 20, wherein the dental treatment apparatus is an ultrasonic dental scaler.

23. The foot switch device of claim 20, wherein the foot switch is used to control the operation of an ultrasonic dental scaler in a wireless, remote control system.

24. The foot switch device of claim 20, wherein the foot switch is used to control the operation of an ultrasonic dental scaler in a hard-wired system.

25. The foot switch device of claim 20, wherein the foot switch is used to control the operation of a medical treatment apparatus.

* * * * *